United States Patent
Terajima et al.

(10) Patent No.: US 8,263,521 B2
(45) Date of Patent: Sep. 11, 2012

(54) PROCESS FOR PRODUCING BISPHENOL A

(75) Inventors: Takashi Terajima, Sodegaura (JP); Yuko Maruyama, Sodegaura (JP); Toshihiro Takai, Sodegaura (JP); Kenji Fujiwara, Sodegaura (JP)

(73) Assignee: Mitsui Chemicals, Inc., Tokyo (JP)

( * ) Notice: Subject to any disclaimer, the term of this patent is extended or adjusted under 35 U.S.C. 154(b) by 0 days.

(21) Appl. No.: 12/981,133

(22) Filed: Dec. 29, 2010

(65) Prior Publication Data

US 2011/0092744 A1    Apr. 21, 2011

Related U.S. Application Data

(62) Division of application No. 10/571,134, filed as application No. PCT/JP2004/012634 on Sep. 1, 2004.

(30) Foreign Application Priority Data

Sep. 10, 2003    (JP) .................................. 2003-317759

(51) Int. Cl.
| | |
|---|---|
| B01J 37/30 | (2006.01) |
| B01J 21/00 | (2006.01) |
| B01J 23/00 | (2006.01) |
| B01J 25/00 | (2006.01) |
| B01J 29/00 | (2006.01) |
| B01J 31/00 | (2006.01) |

(52) U.S. Cl. .......... 502/159; 502/11; 502/100; 502/150; 502/168

(58) Field of Classification Search .................. 502/159, 502/11, 100, 150, 168
See application file for complete search history.

(56) References Cited

U.S. PATENT DOCUMENTS

| | | | | |
|---|---|---|---|---|
| 3,342,755 | A * | 9/1967 | Calmon et al. .................. | 521/33 |
| 5,395,857 | A * | 3/1995 | Berg et al. ........................ | 521/33 |
| 6,329,556 | B1 * | 12/2001 | Sakura et al. .................. | 568/728 |
| 6,653,513 | B1 * | 11/2003 | Iwahara ........................ | 568/728 |
| 2002/0123534 | A1 * | 9/2002 | Lundquist ........................ | 521/25 |
| 2003/0091886 | A1 * | 5/2003 | Tanioka et al. .................. | 429/33 |

FOREIGN PATENT DOCUMENTS

| | | |
|---|---|---|
| EP | 0 318 833 | 11/1988 |
| EP | 1 179 550 A1 | 2/2002 |
| EP | 1 222 960 A2 | 7/2002 |
| JP | 45-10337 B | 4/1970 |
| JP | 46-19953 B | 6/1971 |
| JP | 1-146912 A | 6/1989 |
| JP | 6-320009 A | 1/1991 |
| JP | 05-097741 A | 4/1993 |
| JP | 2000-128819 A | 5/2000 |
| JP | 2001-348349 | 12/2001 |
| JP | 2003-119222 | 4/2003 |
| JP | 2003-119225 | 4/2003 |
| JP | 2004-55165 | 2/2004 |
| WO | WO 00/00454 | 6/2000 |

OTHER PUBLICATIONS

Ming Li et al., "Synthesis and Physical Properties of Sulfonated Syndiotactic Polystyrene Ionomers," Polymer International, vol. 50, pp. 421-428 (2001).
Orler et al., "Crystallization of Lightly Sulfonated Syndiotactic Polystyrene Ionomers," Polymer Preprints, vol. 34, pp. 852-853 (1993).
Su et al., "Spectroscopic and Thermal Studies of Sulfonated Syndiotactic Polystyrene," Macromolecules, vol. 27, pp. 287-291 (1994).

* cited by examiner

*Primary Examiner* — James McDonough
(74) *Attorney, Agent, or Firm* — Birch, Stewart, Kolasch & Birch, LLP

(57) ABSTRACT

The present invention provides a process for producing bisphenol A by reacting phenol with actone, wherein reaction is performed at higher temperatures while maintaining high selectivity, and thus high productivity is obtained. The invention relates to a cation-exchange resin, wherein a cation-exchange group is introduced into a syndiotactic polystyrene polymer and the amount of acid is 0.8 milliequivalent/g or more, to a catalyst comprising the cation-exchange resin, and to a process for producing bisphenol A using a cation-exchange resin catalyst.

11 Claims, No Drawings

PROCESS FOR PRODUCING BISPHENOL A

The present application is a Divisional of co-pending application Ser. No. 10/571,134, filed on Mar. 9, 2006, for which priority is claimed under 35 U.S.C. §120. Application Ser. No. 10/571,134 is a 371 national phase application of PCT/JP2004/12634 filed Sep. 1, 2004 which claims priority to Application No. 2003-317759, filed in Japan on Sep. 10, 2003. All of the above-identified applications are hereby incorporated by reference in their entirety.

TECHNICAL FIELD

The present invention relates to a catalyst comprising a cation-exchange resin with a polystyrene polymer skeleton.

The present invention also relates to a process for producing bisphenol A. More specifically, the invention relates to a process for producing bisphenol A by reacting acetone with phenol in the presence of a cation-exchange resin catalyst.

BACKGROUND ART

Bisphenol A [2,2-bis(4-hydroxyphenyl)propane] is usually produced by reacting phenol with acetone in the presence of a homogeneous acid or a solid acid catalyst. The reaction mixture includes unreacted acetone, unreacted phenol, water and other by-products formed by the reaction, in addition to bisphenol A. The main component of the by-products is 2-(2-hydroxyphenyl)-2-(4-hydroxyphenyl)propane (hereinafter, referred to as o,p'-BPA), and in addition, it includes trisphenol, a polyphenol compound, a chroman compound, colored impurities and the like.

Examples of a homogeneous acid to be used as a catalyst, include hydrochloric acid, sulfuric acid and the like. In the case where the homogeneous acid is used, since it is possible to proceed the reaction while precipitating crystals of an adduct of phenol with bisphenol A by reacting them at lower temperatures, bisphenol A can be produced with a high conversion of acetone and a high selectivity by decreasing the amount of the by-produced o,p'-BPA as an isomer thereof. However, the catalyst of the homogeneous acid such as hydrochloric acid requires a process for removing the catalyst from a reaction mixture or for neutralizing the catalyst, and thus the operation becomes complicated. Homogeneous dissolution of the acid in the reaction solution further causes corrosion of an apparatus or the like used in the reaction. Therefore, the reaction apparatus should use expensive and anti-corrosive materials, thus being uneconomical.

As a solid acid catalyst, a sulfonic acid-type cation-exchange resin is usually used. The reaction for producing bisphenol A essentially proceeds only with an acid catalyst, but if such a solid acid catalyst is used, the process in which acetone diffuses from the surface of the catalyst particles to an active site on the catalyst is involved, and thus the reaction rate is low. Thus, there is a general method used for improving the catalytic activity and the selectivity by allowing a compound containing a mercapto group to coexist in the reaction system (For example, JP-B Nos. 45-10337, 46-19953, etc.).

Further, it is proposed in JP-A No. 62-178532 to use a sulfonic acid-type cation-exchange resin in a fine particle or a fine powder having an effective diameter of 0.3 mm or less for obtaining a sufficient reaction conversion.

Various improvements on the structure of a resin product, which is the base material of a sulfonic acid-type cation-exchange resin, have been made. The sulfonic acid-type cation-exchange resin is a resin obtained by sulfonating a styrene-divinylbenzene copolymer which is obtained by radically copolymerizing styrene and divinylbenzene. The divinylbenzene in polymerization does not only prevent a polystyrene chain from dissolving in an organic solvent, but the content thereof is also an important factor in controlling the size of a pore, i.e., the size of a gel micropore within the sulfonic acid-type cation-exchange resin formed by capturing a polar solvent, or the mechanical strength of the sulfonic acid-type cation-exchange resin.

In other words, a sulfonic acid-type cation-exchange resin with a low content of divinylbenzene has a high catalytic activity due to a large gel micropore, but the mechanical strength is low. In addition, in the case where the content thereof is high, the mechanical strength increases, but the gel micropore size decreases, which causes decreased activity. JP-A Nos. 5-97741 and 6-320009 describe a method which complements the respective defects by simultaneous filling a sulfonic acid-type cation-exchange resin having a low content of divinylbenzene and a sulfonic acid-type cation-exchange resin having a high content of divinylbenzene into a reactor. Further, it is reported in WO 00/00454 that an improvement on a reaction conversion, which suggests a sulfonic acid-type cation-exchange resin having large gel micropores by using large molecules such as divinylbiphenyl instead of divinylbenzene.

The sulfonic acid-type cation-exchange resin in these methods described above comprises as a base material, atactic polystyrene which is obtained by radically copolymerizing styrene and a polyvinyl aromatic compound such as divinylbenzene. Since the atactic polystyrene is an amorphous resin without having a sharp melting point, a commercially available ion-exchange resin comprising the atactic polystyrene having a sulfone group introduced thereinto has room for improvement in heat resistance and is thus known to generate an effluent when it is used under the heating condition of 80° C. or higher. Thus, this causes problems such as deterioration in mechanical strength, decrease in the activity due to clogging of gel micropores, and deterioration over a prolonged period, and thereby there is an obstacle in using thereof at higher temperatures.

In order to overcome such problems, a method has been used which increases the degree of crosslinking and improves heat resistance in an atactic polymer chain. Since the diffusion within the ion-exchange resin particles is extremely lowered as the degree of crosslinking is increased, a large hole referred to as a "macropore" is formed within the particles by a physical treatment in order to improve the diffusion within the particles.

However, in the case where an ion-exchange resin having this macropore adsorbs a molecule having high polarity, such as water, a crosslinked structure tends to inhibit the bulge of particles caused by the swelling, which eventually collapses when it can no longer endure the swelling. Therefore, the development of a heat-resistant ion-exchange resin, which can be treated with an aqueous solvent, is demanded.

It is described in U.S. Pat. No. 3,342,755 that halogen is substituted for hydrogen on the tertiary carbon adjacent to the benzene ring of the styrene moiety in order to overcome the above described problem. However, the substitution of halogen for hydrogen leads to elution of chlorine from the resin, and thus a new problem occurs of incorporating halogen into a reaction mixture.

Further, as a highly heat-resistant ion-exchange resin, a perfluorosulfonic acid-based resin such as nafion is known, in which the maximum amount of acid is about 1.0 milliequivalent/g. Since this polymer skeleton is formed by copolymerization of tetrafluoroethylene and a trifluorovinyl alcohol derivative, an introduction exceeding a given amount of the trifluorovinyl alcohol derivative is problematic in terms of the polymerization technologies, which means that it is impossible to increase the amount of acid.

Further, it is described in the respective papers of Polymer Preprints, Vol. 34, p. 852 (1993), Macromolecules, Vol. 27, p. 287 (1994), Polymer International, Vol. 50, p. 421 (2001) or the like, a process for synthesizing a crystalline polymer containing a sulfone group, in which a sulfone group is introduced into syndiotactic polystyrene, and then crystallized. It is believed that it is necessary to remarkably suppress the amount of acidic functional groups to be introduced, in order to crystallize the sulfonated syndiotactic polystyrene later. Therefore, in this example, the maximum amount of acid is only 1.0 milliequivalent/g, thus being inadequate for a practical catalyst use.

As such, any ion-exchange resin product which has heat resistance and a high amount of acid, and can be used as a catalyst has not been exemplified. If an ion-exchange resin having heat resistance and a high amount of acid can be developed, the ion-exchange resin can be used as a solid catalyst at a high temperature in the reaction using a conventional ion-exchange resin at a low temperature or using a mineral acid as a catalyst, for example, the hydration of isobutene and propylene, the synthesis of bisphenol A from phenol and acetone, the synthesis of methylenedianiline from aniline and formaldehyde, and the like, thus it being an extremely useful catalyst in the industry.

[Patent Document 1] U.S. Pat. No. 3,342,755
[Patent Document 2] JP-A No. 2004-55165
[Non-Patent Document 1] Polymer Preprints, Vol. 34, p. 852 (1993)
[Non-Patent Document 2] Macromolecules, Vol. 27, p. 287 (1994)
[Non-Patent Document 3] Polymer International, Vol. 50, p. 421 (2001)

DISCLOSURE OF THE INVENTION

Problems to be Solved by the Invention

The present invention provides a cation-exchange resin catalyst comprising a polystyrene cation-exchange resin, which has excellent heat resistance and a sufficient amount of acid. Further, the invention provides a process for producing bisphenol A by reacting phenol with acetone, wherein a high heat resistance cation-exchange resin is used as a catalyst in order to solve the above described problems, reaction is performed at higher temperatures while maintaining high selectivity, and as a result, high productivity is obtained.

Means for Solving the Problems

The present inventors have conducted extensive studies to solve the problems, and as a result, they have found that by using a cation-exchange resin which can be obtained by introducing an acidic functional group into a crystalline polymer as a catalyst, a reaction can be performed at higher temperatures without deteriorating the activity, selectivity and durability, and thereby bisphenol A can be obtained with high productivity. Thus, they have completed the invention.

In other words, the invention relates to a cation-exchange resin catalyst as follows:

(1) A cation-exchange resin catalyst comprising a cation-exchange resin, wherein a cation-exchange group is introduced into a syndiotactic polystyrene polymer, and the amount of acid is 0.8 milliequivalent/g or more.

Furthermore, hereinbelow, the preferable embodiments and the production processes for the cation-exchange resin catalyst of the invention will be described.

(2) The cation-exchange resin catalyst as described in (1) above, wherein the crystallinity is 5% or more.

(3) The cation-exchange resin catalyst as described in (1) above, wherein the syndiotacticity of the polystyrene polymer is 70% or more.

(4) The cation-exchange resin catalyst as described in (1) above, wherein the catalyst is used in the reaction of phenol and acetone to produce bisphenol A.

(5) A process for producing bisphenol A by reacting phenol with acetone, wherein the cation-exchange resin catalyst as described in (1) above is used as a catalyst.

Effects of the Invention

According to the present invention, a cation-exchange resin catalyst, which has a high amount of acid and excellent activity, and can be used at a high temperature, is provided.

According to the process of the invention, bisphenol A can be produced with high yield and selectivity, and bisphenol A can be produced with remarkably excellent in safety, processability and economic aspects.

BEST MODE FOR CARRYING OUT THE INVENTION

The cation-exchange resin catalyst of the present invention is produced by subjecting the styrene polymer to chemical treatment for introduction of an acidic functional group.

The styrene polymer includes α or β substituted polystyrenes such as polystyrene and poly(α-methylstyrene), and phenyl substituted polystyrenes such as poly(p-methylstyrene). Among these, unsubstituted polystyrene is preferred.

For example, syndiotactic polystyrene in which the phenyl groups which are the side-chain with respect to the main chain formed by a carbon-carbon bond of the polystyrenes obtained by the polymerization of a styrenic monomer alone or the copolymerization of a styrenic monomer and a polyvinyl aromatic compound, are alternately located in the opposite direction, and isotactic polystyrene in which the phenyl groups are located in the same direction are preferable from the viewpoint that they have crystallinity, and syndiotactic polystyrene are more preferable from the viewpoint that it rapidly crystallizes.

Syndiotactic polystyrene may be commercially available one, or may be a polymer obtained by polymerization of a styrenic monomer alone or a polymer obtained by copolymerization of a styrenic monomer and a polyvinyl aromatic monomer. The polymerization method is not particularly limited, but in either cases of using a polymer obtained by the polymerization of a styrenic monomer alone or of using a polymer obtained by the copolymerization of a styrenic monomer and a polyvinyl aromatic monomer, a polymer having high stereoregularity can be obtained by using the method as disclosed in, for example, JP-A No. 8-151492, JP-A No. 8-151414, JP-A No. 8-143729, JP-A No. 8-134122, JP-B No. 7-77790, JP-B No. 7-57767, JP-B No. 7-55994, or the like.

The tacticity indicating the stereoregularity of syndiotactic polystyrene can be measured by a 13C-NMR method and can be represented by the existence ratios of the plural consecutive constitutional units, for example, a dyad in the case of where two constitutional units exist, a triad in the case of where three constitutional units exist, and a pentad in the case of where five constitutional units exist, and in the racemic dyad, the ratio is preferably 70% or more, and more preferably 75% or more.

Other ones with stereostructures such as isotatic polymers may be mixed with the syndiotactic polystyrene as long as they do not adversely affect the scope of the invention.

The polymer used in the invention may have a crosslinked structure. The crosslinked structure means the structure such that the main chain or side chain of a polymer molecule is linked with the main chain or side chain of another polymer molecule via a crosslinking structure by means of any kind of methods for introducing the crosslinked structure. For example, if styrene having one vinyl group and divinylbenzene which is polyvinyl aromatics are copolymerized, a main chain of the polymer can be generated, as well as a crosslinked structure can be introduced. Further, a polymer having no crosslinked structure may be crosslinked later by the method as disclosed in JP-A No. 2002-363116.

In the case of using a polymer obtained by the copolymerization of a styrenic monomer and a polyvinyl aromatic monomer, the degree of crosslinking, which is represented by, for example, (weight of polyvinyl aromatic monomer)/(weight of total monomers), is from 0.01% to 20% (inclusive), preferably from 0.1% to 15% (inclusive), and particularly preferably from 0.1% to 10% (inclusive).

Elution of the thus obtained ion-exchange resin is suppressed, and its physical strength is enhanced while maintaining the diffusibility of the material in the ion-exchange resin. As a result, it is possible to maintain its catalytic activity over a prolonged period.

The styrenic monomer used includes styrene and substituted styrene such as α-methylstyrene, vinyltoluene, vinylxylene, ethylvinylbenzene, vinylnaphthalene, vinylbiphenyl, methylvinylbiphenyl and the like, and preferred is styrene.

The polyvinyl aromatic monomer includes, for example, divinylbenzene, divinyltoluene, divinylchlorobenzene, diallyphthalate, divinylnaphthalene, divinylxylene, divinylethyl benzene, trivinylnaphthalene, polyvinylanthracene, divinylphenanthrene, divinylbiphenyldivinyl terphenyl, divinyl diphenylmethane, divinyl diphenylmethane and the like, and preferred is divinylbenzene.

The styrenic monomer and the polyvinyl aromatic monomer can be used in any combination, but in order to sufficiently perform the crosslinking, it is important to adjust the reactivity of polymerization reactions with a combination of the vinyl groups, as in styrene and divinylbenzene.

The invention is characterized in that the polymer is first crystallized by heat treatment or other methods, and an acidic functional group is later introduced thereto from the exterior surface of the polymer particle. With this method, the acidic functional group can be introduced in any proportion without adversely affecting the crystallinity of the whole particle.

In other words, if the operation is sufficiently performed during the crystallization process, a polymer having high crystallinity can be obtained, and with a simple and easy operation, a polymer having low crystallinity can be obtained. Further, even when an acidic functional group is introduced into these polymers, the amount of acidic functional group to be introduced can be controlled by selection of the reaction condition and the kind of electrophilic reagents. As such, the crystallinity and the amount of acidic functional group can have any value.

The method for crystallizing a polymer is not particularly limited and employs a well-known method, but a method for performing heat treatment of a crystalline polymer is convenient, which is preferable. For the heat treatment, mention may be made of, for example, a method of heating a polymer to its melting point or higher and then cooling the polymer, a method of heating a polymer to its melting point or lower, maintaining the polymer at that temperature and then cooling the polymer, a method of dissolving or dispersing a polymer in a solvent, heating the polymer, and then cooling the polymer, and the like, and any such method may be used. In order to enhance the heat resistance of the obtained ion-exchange resin, the crystallinity as determined by an X-ray process is preferably from 5% to 50% (inclusive), and more preferably from 10% to 50% (inclusive). The X-ray process for determining the crystallinity of a polymer is a generally known process, and described in "Kobunshi Jikkengaku, Vol. 17, Solid Structure of Polymer II, p. 313, Kyoritsu Shuppan (1984)", etc.

According to the invention, the acidic functional groups to be introduced into the polymer include a carboxyl group, a sulfonic acid group and the like, among which the sulfonic acid group is preferable due to sufficient strength as an acid catalyst, easy introduction by an electrophilic reaction, or the like.

A well-known method can be used for introduction of a sulfonic acid group, and the method includes, for example, a method wherein a predetermined amount of a reagent such as sulfuric acid, acetyl sulfuric acid, fuming sulfuric acid and chlorosulfuric acid is added for sulfonation in the liquid phase in the presence of a swelling agent or a solvent, a method wherein a sulfonating agent such as sulfur trioxide is contacted with a polymer in the gas phase for sulfonation, and the like. From the viewpoint of the sulfonation rate, a method for sulfonation in the liquid phase is preferred.

The solvent or swelling agent used in the sulfonation in the liquid phase is not particularly limited as long as it does not react with a sulfonating reagent, but those having too high solubility in a polystyrene polymer might adversely affect the crystallinity of the polymer. In addition, when the affinity with the polystyrene polymer is too low, sulfonation may not proceed sufficiently. The swelling agent or the solvent can be suitably chosen in consideration of these points, but in the case of using polystyrene for the polystyrene polymer, it is preferable to use a high polarity solvent such as nitrobenzene, glacial acetic acid, 1,4-dioxane and petroleum ether, because sulfonation proceeds from the surface of the polymer particles.

In order to obtain a sufficient function as a catalyst, the amount of acid of the ion-exchange resin after introduction of an acidic functional group is preferably 0.8 milliequivalent/g or more, and more preferably 1.1 milliequivalent/g or more. Further, the amount of acid of the ion-exchange resin can be determined by stirring 0.2 g of a proton type dry resin in 100 ml of a 10% aqueous NaCl solution for one hour and back-titrating the whole amount of the filtrate with a 0.05 N aqueous NaOH solution.

As the ion-exchange resin obtained in the invention, an ion-exchange resin which generates a lower amount of the eluate, as compared with a conventional one in the use of the heating condition, can be obtained. For example, when 50 g of water and 2 g of the ion-exchange resin are stirred at 130° C. for 18 hours, the elution of the acid components into water is preferably 1.5% or less, and more preferably 1.1% or less.

The forms of such ion-exchange resin are defined in the stages of polystyrene obtained in polymerization. In other words, if the acidic functional group is introduced as the powder obtained in polymerization, an ion-exchange resin in the powder form can be obtained. On the other hand, in the stages of polystyrene, a particle or a sheet may be formed by a well known method or a fibrous form may be obtained after spinning, and if an acidic functional group is introduced to the formed product as a raw material, an ion-exchange resin maintaining the shape of polystyrene can be obtained. For the form of polystyrene, a large powder or particle form having a large specific surface area is preferred from the points of easy introduction of the acidic functional group and excellent catalytic activity.

The reaction for producing Bisphenol A essentially proceeds with an acid catalyst only, but typically a method for improving the catalytic activity and the selectivity by allowing a mercapto group-containing compound coexist therewith as a cocatalyst, can be adopted. Also, in the invention, it is preferable for allowing a mercapto group-containing compound to coexist. Such methods include a method wherein a small amount of a mercapto group-containing compound such as alkyl mercaptan is mixed with a mixture of phenol and acetone which are raw materials, and the resultant mixture is used, a method wherein a mercapto group-containing compound is bound to an acidic functional group of a cation-exchange resin, and the like, and any such method may be used.

The mercapto group-containing compound to be mixed with the mixture of phenol and acetone is not particularly limited in the structure, as long as it contains a mercapto group in its molecule, and it includes, for example, mercapto alkyl groups such as a mercaptomethyl group, a 2-mercaptoethyl group and a 3-mercapto-n-propyl group, alicyclic hydrocarbon groups such as a 4-mercaptocyclohexyl group and a 4-mercaptomethyl cyclohexyl group, mercapto aromatic groups such as a p-mercaptophenyl group and a p-mercaptomethylphenyl group, and the like. Further, these aromatic, aliphatic or alicyclic hydrocarbon groups may be hydrocarbon groups having a substituent such as a halogen atom, an alkoxy group, a nitro group and a hydroxyl group, in addition to the mercapto group. The amount of this mercapto group-containing compound to be added to the mixture of phenol and acetone is preferably in the range of 100 wtppm to 5 wt %. By this, it is possible to exhibit the cocatalyst effect to a maximum extent with a small amount of a cocatalyst.

The mercapto group-containing compound to be bound to a part of the acidic functional group of the cation-exchange resin is not particularly limited, but the compound may be any one which forms an ionic bond with the acidic functional group of the cation-exchange resin. This compound includes mercapto alkylamines such as 2-mercaptoethylamine (cysteamine), 3-mercaptopropylamine and N,N-dimethyl-3-mercaptopropylamine, mercaptoalkyl pyridines such as 3-mercaptomethyl pyridine, 3-mercaptoethyl pyridine and 4-mercaptoethyl pyridine, thiazolidines such as thiazolidine, 2,2-dimethylthiazolidine, 2-methyl-2-phenylthiazolidine and 3-methylthiazolidine, and the like. The ratio for the acidic functional group to be bound to the mercapto group-containing compound is 2 to 50%, and preferably 5 to 30% of the total sulfonic acid groups of the sulfonic acid-type cation-exchange resin. By this, it is possible to exhibit the cocatalyst effect to a maximum extent without causing the decrease in the activity due to the decrease in an amount of acid. For the method wherein a mercapto group-containing compound is bound to a cation-exchange resin, there may be used a conventionally known method as disclosed in JP-B No. 46-19953, or the like.

In the invention, for phenol to be used as a raw material for producing bisphenol A, a generally available industrial phenol can be used. The industrial phenol includes one prepared by a cumene method, a toluene oxidation method, or the like, any of which may be used. Generally, phenol having a purity of 98% or more is commercially available. Such the industrial phenol may be used as it is in the synthesis reaction of bisphenol A, but preferably phenol which is preliminarily treated with a strong acid-type cation-exchange resin in a continuous or batch mode before carrying out the reaction at a treatment temperature of 50 to 120° C. during a contact time of 5 minutes to 10 hours, is used. Even more preferably, one obtained by the process wherein the industrial phenol is brought into contact with a strong acid-type cation-exchange resin as described above and is then subjected to a distillation treatment under the condition of a normal pressure to a reduced pressure of 10 mmHg, at a temperature of 70 to 200° C., is used.

Acetone used in the invention is not particularly limited, but it may be a commercially available industrial acetone. Generally, acetone having a purity of 99% or more is available.

The amounts (quantitative ratios) of phenol and acetone, used as raw materials, to be used, are not particularly limited, but the molar ratio of phenol/acetone is recommended preferably in the range of 0.1 to 100, and more preferably in the range of 0.5 to 50. If the amount of phenol is too small, it is difficult to accomplish a high conversion of acetone as a raw material, if the amount of phenol is too large, the reactor becomes unreasonably larger because phenol is used as the higher amount than required, and moreover, massive circulation of phenol is also required, even though a high conversion of acetone can be accomplished. Thus, efficient production cannot be accomplished.

In the invention, the reaction temperature is not particularly limited, but it is preferably in the range of 0 to 300° C., and more preferably in the range of 30 to 200° C. If the reaction temperature is extremely low, the reaction rate decreases and thus the productivity of a reaction product also decreases. On the other hand, if the reaction temperature is extremely high, an undesirable side reaction, or the like proceeds, thus leading to the increase in the amount of by-products, and to the decrease in stability of phenol and acetone as a raw material and further bisphenol A as a product, and the reaction selectivity. Therefore, it is not economical.

The reaction can be carried out under any of a reduced pressure, an applied pressure and a normal pressure. From the viewpoint of the reaction efficiency (reaction efficiency per unit volume), it is not preferable to carry out the reaction under too low of pressure. Usually, the pressure for carrying out the reaction is preferably in the range of 0.1 to 200 atm, and more preferably in the range of 0.5 to 100 atm. Of course, the invention is not limited to such pressure ranges.

In addition, when carrying out the invention, the amount of the catalyst to be used is not particularly limited, but for example, when carrying out the reaction in a batch mode, it is recommended to carry out the invention such that the amount of the catalyst is preferably in the range of 0.001 to 200% by weight, and more preferably in the range of 0.1 to 50% by weight with respect to phenol as a raw material.

When carrying out the invention, it is possible to add a solvent or gas which is inert to a catalyst and a reaction reagent in the reaction system, which can be used in the diluted state. Specifically, aliphatic hydrocarbons such as methane, ethane, propane, butane, hexane and cyclohexane, and an inert gas such as nitrogen, argon and helium, and if necessary, hydrogen can be used as a diluent.

When carrying out the invention, the method can be carried out in any of a batch, semi-batch or continuous flow system. It can be carried out in any of a liquid phase, a gas phase, a gas-liquid mixed phase. Preferably, from the viewpoint of the reaction efficiency, it is recommended that the reaction is carried out in the liquid phase. For a way for charging a catalyst, various kinds of ways using, for example, a fixed bed, a fluidized bed, a suspended bed and a plate fixed bed can be employed, any of which can be used.

The reaction time (retention time or catalytic contact time in the flow system) is not particularly limited, but it is usually 0.1 second to 30 hours, and preferably 0.5 second to 15 hours. After the reaction, the reaction product can be separated and recovered from the catalysts, or the like, by a separation method such as filtration, extraction and distilling-off. Bisphenol A as a target product can be separated, purified and obtained from the reaction mixture separated and recovered by performing a sequential treatment of solvent extraction, distillation, alkali treatment, acid treatment and the like or an ordinary separation and purification method suitably combining them. In addition, unreacted raw materials can be recovered and recycled into the reaction system for use.

In the case of a batch reaction, the catalyst which is separated and recovered from the reaction product after the reaction, can be used as it is, or partially or wholly reproduced to be repeatedly used for the reaction. In the case of carrying out the reaction in a fixed bed or a fluidized bed flow system, if the catalyst is provided to the reaction and thereby a part or all of the catalysts is inactivated or is deteriorated in the activity, the reaction is interrupted, and thereafter the catalyst can be reproduced and then provided to the reaction. Alternatively, a part of the catalyst can be withdrawn continuously or intermittently and reproduced, and then recycled to the reactor for re-use. Further, a fresh catalyst can be intermittently supplied to the reactor. When carrying out the reaction in a moving-bed flow system, the catalyst can be separated, recovered and, if necessary, reproduced, as in the batch reaction.

EXAMPLES

Hereinbelow, the present invention will be described in more detail in reference to Examples. However, the invention is not intended to be limited to Examples.

Example 1

(1) Synthesis of Styrenic Polymer 180 ml of toluene, 45 ml of styrene, 24 ml of a 10% methyl aluminoxane/toluene solution, and 3.6 ml of a 0.5% cyclopentadienyltitanium trichloride/toluene solution were charged and reacted at 50° C. for 2 hours under a nitrogen atmosphere. Thereafter, the recovered polymer was washed and dried. By $^{13}$C-NMR measurement of the obtained polymer, it was confirmed that this polymer was syndiotactic polystyrene. Further, peaks of Tc (crystallization) could be found at 222° C. by DSC measurement of 5 mg of this polymer at 10° C./min.

(2) Heat Treatment of Styrenic Polymer

The sufficiently dried styrenic polymer was maintained at 200° C. for 4 hours under a nitrogen atmosphere and then slowly cooled under a nitrogen atmosphere.

(3) Sulfonation of Styrenic Polymer 130 g of nitrobenzene, 10 g of styrenic polymer which had been heat-treated in (2), and 50 g of sulfuric acid were charged and reacted at 80° C. for 3 hours. After the reaction, the resin fraction was separated by filtration, sufficiently washed with ion-exchange water and further dried under reduced pressure at 80° C. for 24 hours to obtain a cation-exchange resin 1. The amount of acid of the obtained cation-exchange resin 1 was 1.1 milliequivalents/g. Further, peaks were found at 2θ of 6.7, 11.7, 13.5 and 20.4° by XRD measurement of this cation-exchange resin 1 with a CuKα-ray. The crystallinity was 21%.

Example 2

130 g of nitrobenzene, 10 g of styrenic polymer which had been heat-treated in (2) of Example 1, and 50 g of sulfuric acid were charged and reacted at 80° C. for 6 hours. After the reaction, the resin fraction was separated by filtration, sufficiently washed with ion-exchange water and further dried under reduced pressure at 80° C. for 24 hours to obtain a cation-exchange resin 2. The amount of acid of the obtained cation-exchange resin 2 was 1.7 milliequivalents/g. Further, peaks were found at 20 of 6.7, 11.7, 13.5 and 20.4° by XRD measurement of this cation-exchange resin 2 with a CuKα-ray. The crystallinity was 14.9%.

Example 3

The procedure was performed under the same conditions as in Example 1, except that a combination of 45 ml of styrene and 0.7 ml of 80% divinylbenzene was used instead of 45 ml of styrene, to obtain cation-exchange resin 3. By $^{13}$C-NMR measurement of the styrenic polymer prior to heat treatment, it was confirmed that this polymer was syndiotactic polystyrene. Further, peaks of Tc (crystallization) were found at 217° C. by DSC measurement of 5 mg of the styrenic polymer prior to heat treatment at 10° C./min. The amount of acid of the cation-exchange resin 3 was 3.7 milliequivalents/g. Further, peaks were found at 2θ of 6.7, 11.7, 13.5 and 20.4° by XRD measurement of this cation-exchange resin 3 with a CuKα-ray. The crystallinity was 10.5%.

Comparative Example 1

(1) Sulfonation of Styrenic Polymer 130 g of nitrobenzene, 10 g of styrenic polymer which had been obtained in (1) of Example 1, and 50 g of sulfuric acid were charged and reacted at 80° C. for 3 hours. After the reaction, the resin fraction was separated by filtration, sufficiently washed with ion-exchange water and further dried under reduced pressure at 80° C. for 24 hours to obtain a cation-exchange resin 4. The amount of acid as measured was 1.1 milliequivalents/g.

(2) Heat Treatment of Cation-Exchange Resin 4

The sufficiently dried cation-exchange resin 4 was maintained at 200° C. for 4 hours under a nitrogen atmosphere and then slowly cooled under a nitrogen atmosphere. No clear peak was observed upon XRD measurement of this heat-treated cation-exchange resin 4 with a CuKα-ray.

Comparative Example 2

Heat treatment was performed in the same manner as in (2) of Example 1, except that Amberlyst 31, which had been sufficiently washed and dried, was used instead of the styrenic polymer. No clear peak was observed upon XRD measurement thereof with a CuKα-ray.

Example 4

Into a 70 ml pressure-resistant reactor, 50 g of distilled water, and 2 g of the cation-exchange resin 1 produced in Example 1 were charged, and pressurized with nitrogen gas under 5 kg/cm² of a gauge pressure inside the reactor, and then heated with stirring at 130° C. for 18 hours. Thereafter, the resultant was cooled to room temperature. After the pressure discharge, all the contents were taken out, and separated by filtration with a membrane filter having a pore diameter of 0.1 μm. Then, the amount of acids of the filtrate and the residue were measured, respectively. As a result, about 1.1% of the amount of acid to be put was detected in the filtrate, and the remaining amounts were detected in the residue.

Example 5

The same procedure as in Example 4 was performed, except that the cation-exchange resin 2 produced in Example 2 was used instead of the cation-exchange resin 1. As a result, about 1.0% of the amount of acid to be put was detected in the filtrate, and the remaining amounts were detected in the residue.

Example 6

The same procedure as in Example 4 was performed, except that the cation-exchange resin 3 produced in Example 3 was used instead of the cation-exchange resin 1. As a result, about 0.7% of the amount of acid to be put was detected in the filtrate, and the remaining amounts were detected in the residue.

Comparative Example 3

The same procedure as in Example 4 was performed, except that the cation-exchange resin 4 produced in Comparative Example 1 was used instead of the cation-exchange resin 1. As a result, about 3.0% of the amount of acid to be put was detected in the filtrate, and the remaining amounts were detected in the residue.

Comparative Example 4

The same procedure as in Example 4 was performed, except that Amberlyst 31, which had been sufficiently washed and dried, was used instead of the cation-exchange resin 1. As a result, about 2.0% of the amount of acid to be put was detected in the filtrate, and the remaining amounts were detected in the residue.

Example 7

Modification of Cation-Exchange Resin 5 g of the cation-exchange resin 3 obtained in Example 3 was dispersed in 100 ml of ion-exchange water, and an arbitrary amount of a 0.85% aqueous solution of aminoethanethiol hydrochloride was added dropwise with stirring for 1 hour. Thereafter, the resultant was stirred at a room temperature for 5 hours, and then the resin fraction was separated by filtration, sufficiently washed with ion-exchange water and further dried under reduced pressure at 80° C. for 24 hours to obtain a modified cation-exchange resin A. (Here, the obtained modified cation-exchange resin A was a modified cation-exchange resin in which 35% of the sulfonic acid groups bound to aminoethanethiol.)

Example 8

Into a 70 ml pressure-resistant reactor, 1.59 g of acetone, 28.41 g of phenol and 0.75 g of the cation-exchange resin A produced in Example 7 were charged, and pressurized with nitrogen gas under 5 kg/cm² of a gauge pressure inside the reactor, and then heated with stirring at 75° C. for 2 hours. After completion of the reaction, the resultant was cooled to room temperature. After the pressure discharge, the reaction solution was taken out, and subjected to quantitative analysis by means of liquid chromatography. The results are shown in Table 1.

Example 9

Under the same conditions as in Example 8, except that the amount of phenol to be charged was changed to 20.66 g, and the reaction temperature was changed to 85° C., the reaction was performed. The results are shown in Table 1.

Example 10

Under the same conditions as in Example 8, except that the amount of phenol to be charged was changed to 12.91 g, and the reaction temperature was changed to 100° C., the reaction was performed. The results are shown in Table 1.

TABLE 1

| | Amount of acetone to be charged (g) | Amount of phenol to be charged (g) | Reaction temperature (° C.) | Conversion of acetone (%) | Selectivity to bisphenol A (%) |
|---|---|---|---|---|---|
| Example 8 | 1.59 | 28.41 | 75 | 65.2 | 92.8 |
| Example 9 | 1.59 | 20.66 | 85 | 61.5 | 90.9 |
| Example 10 | 1.59 | 12.91 | 100 | 64.4 | 86.8 |

Comparative Example 5

Under the same conditions as in Example 8, except that a modified Amberlyst 31 obtained by ion-exchange of 35% of the sulfonic acid groups of a commercially available Amberlyst 31 with aminoethanethiol was used as a catalyst, the reaction was performed. The results are shown in Table 2.

Comparative Example 6

Under the same conditions as in Example 9, except that a modified Amberlyst 31 obtained by ion-exchange of 35% of the sulfonic acid groups of a commercially available Amberlyst 31 with aminoethanethiol was used as a catalyst, the reaction was performed. The results are shown in Table 2.

Comparative Example 7

Under the same conditions as in Example 10, except that a modified Amberlyst 31 obtained by ion-exchange of 35% of the sulfonic acid groups of a commercially available Amberlyst 31 with aminoethanethiol was used as a catalyst, the reaction was performed. The results are shown in Table 2.

TABLE 2

| | Amount of acetone to be charged (g) | Amount of phenol to be charged (g) | Reaction temperature (° C.) | Conversion of acetone (%) | Selectivity to bisphenol A (%) |
|---|---|---|---|---|---|
| Comp. Ex. 5 | 1.59 | 28.41 | 75 | 62.8 | 91.4 |
| Comp. Ex. 6 | 1.59 | 20.66 | 85 | 48.4 | 88.4 |
| Comp. Ex. 7 | 1.59 | 12.91 | 100 | 61.1 | 81.1 |

Example 11

The modified cation-exchange resin A which had been used as a catalyst in Example 10 was taken out by filtration after the reaction, the raw material was charged therein again, and the reaction was performed under the same conditions. The results are shown in Table 3.

Example 12

The modified cation-exchange resin A which had been once reused as a catalyst in Example 11 was taken out by filtration after the reaction, the raw material was charged therein again, and the reaction was performed under the same conditions. The results are shown in Table 3.

Example 13

The modified cation-exchange resin A which had been twice reused as a catalyst in Examples 11 and 12 was taken out by filtration after the reaction, the raw material was charged therein again, and the reaction was performed under the same conditions. The results are shown in Table 3.

TABLE 3

|  | Number of times of reuse of catalyst | Amount of acetone to be charged (g) | Amount of phenol to be charged (g) | Reaction temperature (° C.) | Conversion of acetone (%) | Selectivity to bisphenol A (%) |
|---|---|---|---|---|---|---|
| Example 11 | 1st | 1.59 | 12.91 | 100 | 63.5 | 86.5 |
| Example 12 | 2nd | 1.59 | 12.91 | 100 | 65.0 | 87.2 |
| Example 13 | 3rd | 1.59 | 12.91 | 100 | 64.0 | 87.0 |

Comparative Example 8

The modified Amberlyst 31 which had been used as a catalyst in Comparative Example 7 was taken out by filtration after the reaction, the raw material was charged therein again, and the reaction was performed under the same conditions. The results are shown in Table 4.

Comparative Example 9

The modified Amberlyst 31 which had been once reused as a catalyst in Comparative Example 8 was taken out by filtration after the reaction, the raw material was charged therein again, and the reaction was performed under the same conditions. The results are shown in Table 4.

Comparative Example 10

The modified Amberlyst 31 which had been twice used as a catalyst in Comparative Examples 8 and 9 was taken out by filtration after the reaction, the raw material was charged therein again, and the reaction was performed under the same conditions. The results are shown in Table 4.

TABLE 4

|  | Number of times of reuse of catalyst | Amount of acetone to be charged (g) | Amount of phenol to be charged (g) | Reaction temperature (° C.) | Conversion of acetone (%) | Selectivity to bisphenol A (%) |
|---|---|---|---|---|---|---|
| Comp. Ex. 8 | 1st | 1.59 | 12.91 | 100 | 59.5 | 80.0 |
| Comp. Ex. 9 | 2nd | 1.59 | 12.91 | 100 | 57.8 | 80.5 |
| Comp. Ex. 10 | 3rd | 1.59 | 12.91 | 100 | 55.0 | 79.5 |

Example 14

Into a 70 ml pressure-resistant reactor, 1.59 g of acetone, 28.41 g of phenol and 0.75 g of the cation-exchange resin 3 produced in Example 3 were charged, and 3-mercaptopropionic acid was further charged thereto to a concentration of 3000 ppm, and the resultant was pressurized with nitrogen gas under 5 kg/cm$^2$ of a gauge pressure inside the reactor, and then heated with stirring at 75° C. for 2 hours for reaction. After completion of the reaction, the resultant was cooled to room temperature. After the pressure discharge, the reaction solution was taken out, and subjected to quantitative analysis by means of liquid chromatography. The results are shown in Table 5.

Example 15

Under the same conditions as in Example 14, except that the amount of phenol to be charged was changed to 20.66 g, and the reaction temperature was changed to 85° C., the reaction was performed. The results are shown in Table 5.

TABLE 5

|  | Amount of acetone to be charged (g) | Amount of phenol to be charged (g) | Reaction temperature (° C.) | Conversion of acetone (%) | Selectivity to bisphenol A (%) |
|---|---|---|---|---|---|
| Example 14 | 1.59 | 28.41 | 75 | 81.2 | 93.9 |
| Example 15 | 1.59 | 20.66 | 85 | 79.4 | 90.5 |

Comparative Example 11

Under the same conditions as in Example 14, except that a commercially available Amberlyst 31 was used as a catalyst instead of the cation-exchange resin produced in Example 1, the reaction was performed. The results are shown in Table 6.

Comparative Example 12

Under the same conditions as in Example 15, except that a commercially available Amberlyst 31 was used as a catalyst instead of the cation-exchange resin produced in Example 1, the reaction was performed. The results are shown in Table 6.

TABLE 6

|  | Amount of acetone to be charged (g) | Amount of phenol to be charged (g) | Reaction temperature (° C.) | Conversion of acetone (%) | Selectivity to bisphenol A (%) |
|---|---|---|---|---|---|
| Comp. Ex. 11 | 1.59 | 28.41 | 75 | 81.0 | 91.5 |
| Comp. Ex. 12 | 1.59 | 20.66 | 85 | 77.9 | 87.3 |

The invention claimed is:

1. A process for producing bisphenol A by reacting phenol with acetone in the presence of a cation-exchange resin catalyst, said cation-exchange resin catalyst comprising a cation-exchange resin, wherein the cation-exchange resin catalyst is a catalyst obtained by crystallizing a syndiotactic polystyrene polymer, which is obtained by copolymerization of a styrenic monomer and a polyvinyl aromatic monomer, and then introducing an acidic functional group into the polymer on an exterior surface of the polymer particle, the amount of acid is 0.8 milliequivalent/g or more and the crystallinity is from 10% to 50%.

2. The process for producing bisphenol A according to claim 1, wherein the syndiotacticity of the polystyrene polymer is 70% or more.

3. The process for producing bisphenol A according to claim 1, wherein the amount of acid is 1.1 to 3.7 milliequivalent/g.

4. The process for producing bisphenol A according to claim 1, wherein the cation-exchange resin catalyst is a catalyst obtained by crystallizing the syndiotactic polystyrene polymer and then sulfonating the surface of the polymer particle using a high polarity solvent selected from nitrobenzene, glacial acetic acid, 1,4-diozane and petroleum ether to introduce a sulfonic acid group into the polymer.

5. A process for producing the cation-exchange resin catalyst of claim 1, which comprises crystallizing a syndiotactic polystyrene polymer and then introducing a cation-exchange group into the polymer.

6. The process for producing the cation-exchange resin catalyst according to claim 5, wherein the syndiotacticity of the polystyrene polymer is 70% or more.

7. The process for producing the cation-exchange resin catalyst according to claim 5, wherein the catalyst is used in the reaction of phenol and acetone to produce bisphenol A.

8. The process for producing the cation-exchange resin catalyst according to claim 5, wherein the amount of acid is 1.1 to 3.7 milliequivalent/g.

9. The process for producing the cation-exchange resin catalyst according to claim 5, wherein the polystyrene polymer is a polymer obtained by polymerization of a styrenic monomer alone or a polymer obtained by copolymerization of a styrenic monomer and a polyvinyl aromatic monomer.

10. The process for producing bisphenol A according to claim 1, wherein the polyvinyl aromatic monomer is at least one selected from the group consisting of divinylbenzene, divinyltoluene, divinylchlorobenzene, diallyphthalate, divinylnaphthalene, divinylxylene, divinyl ethyl benzene, trivinylnaphthalene, polyvinylanthracene, divinylphenanthrene, divinylbiphenyldivinyl terphenyl, divinyl diphenylmethane and divinyl diphenylmethane.

11. The process for producing bisphenol A according to claim 1, wherein the degree of crosslinking, which is represented by (weight of polyvinyl aromatic monomer)/(weight of total monomers), is from 0.01% to 20%.

* * * * *